(12) United States Patent
Bernhard et al.

(10) Patent No.: US 6,496,727 B1
(45) Date of Patent: Dec. 17, 2002

(54) MEDICAMENT-LOADED TRANSDERMAL RESERVOIR AND METHOD FOR ITS FORMATION

(75) Inventors: Michael I. Bernhard, Summit, NJ (US); Ralph Ewall, Long Valley, NJ (US); Curtis Karl, Somerset, NJ (US); Preston Keusch, Hazlet, NJ (US); Gary Kupperblatt, Belle Mead, NJ (US); Daniel O'Grady, Edison, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 162 days.

(21) Appl. No.: 09/584,453

(22) Filed: May 31, 2000

(51) Int. Cl.[7] .................................................. A61N 1/30
(52) U.S. Cl. ........................................................ 604/20
(58) Field of Search ...................... 604/19, 20; 424/443, 424/446–449

(56) References Cited

U.S. PATENT DOCUMENTS 5,203,768 A * 4/1993 Haak et al. ................... 604/20
5,362,308 A * 11/1994 Chien et al. .................. 604/20

* cited by examiner

*Primary Examiner*—Michael J. Hayes
(74) *Attorney, Agent, or Firm*—Hoffmann & Baron, LLP

(57) ABSTRACT

A transdermal reservoir and method for loading a material into a reservoir includes providing a bibulous reservoir blocking a backing with an interior surface having a patient contact surface with a shape disposed on the interior surface of the backing. A closure is sized and shaped to engage the backing for forming a releasable seal to isolate the bibulous reservoir from the ambient environment. The closure has an inside surface with a section of an absorbent material disposed thereon. When the closure is disposed on the backing, the absorbent material is positioned in intimate physical contact with the reservoir. The method includes applying an aliquot of a material to the absorbent material, placing the closure on the backing so that the absorbent material is in intimate physical contact with the contact surface of the bibulous reservoir and the closure forms the releasable seal with the backing. The reservoir is allowed to stand for a sufficient time to allow the aliquot to be absorbed into the bibulous material thereby loading the reservoir.

25 Claims, 8 Drawing Sheets

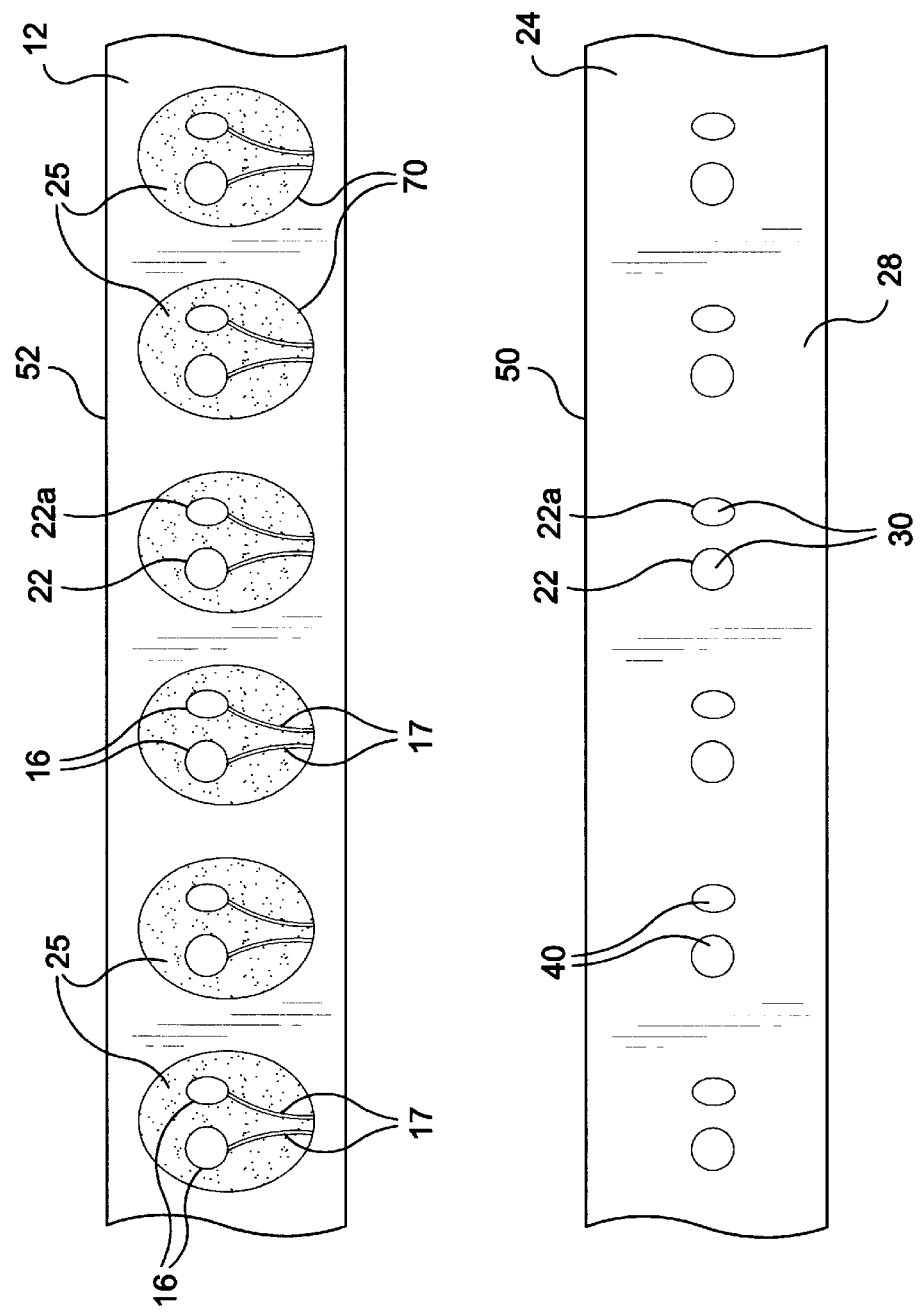

MEDICAMENT-LOADED TRANSDERMAL RESERVOIR AND METHOD FOR ITS FORMATION

FIELD OF INVENTION

The present invention is related to a method of loading a material into a bibulous reservoir useful for drug delivery and more particularly into a method for loading a medicament into an iontophoretic reservoir-electrode and a iontophoretic reservoir-electrode formed by the method.

BACKGROUND

Iontophoretic delivery of a medicament is accomplished by application of a voltage to a medicament loaded reservoir-electrode, sufficient to maintain a current between the medicament loaded reservoir-electrode and a return electrode (another electrode) applied to a patient's skin so that an ionic form of the desired medicament is delivered to the patient.

Shelf storage stability problems for many of the iontophoresis devices reported in the literature require that the medicament be stored separately from the reservoir-electrode until immediately prior to use. Iontophoretic delivery of medicaments is recognized as desirable for many medicaments, but it is not widely used because no devices are commercially available that meet all of the needs of the potential user population. An important requirement for a product to enjoy widespread usage is shelf storage stability. If a drug product is not stable under normal shelf storage conditions, it is unlikely to be a successfully commercialized product because the short shelf life limits the product's utility to most potential users as most of the product's useful life is exhausted during the time required for manufacturing and the distribution process. Thus, determination of shelf storage stability is an important part of a drug product's regulatory approval process. If there are difficulties with storage stability, regulatory approval may be withheld. Often, the reservoir-electrode also is maintained in a dry (unhydrated) condition prior to use also because of the tendency of the active electrode material to undergo physical and chemical changes during shelf storage. The need to store the several components separately has limited the use of iontophoretic devices, since in order to use the device, the reservoir-electrode needs to be charged with the medicament and hydrated either by a practitioner or user immediately prior to use. There are regulatory requirements related to the accuracy and precision of content of a particular drug in an individual dosage form. When a drug dosage form is a tablet, there are specific requirements related to weight variation, dissolution, content and stability. Parenteral dosage forms require concentration assay and stability. Other more complex dosage forms such as transdermal or iontophoretic delivery devices are developing similar standards, but the problems related to loading the devices and the stability of the charged devices are continuing problems.

Several United States Patents disclose devices that attempt to overcome the problem of shelf storage stability and facilitate the preparation of the device for use. U.S. Pat. No. 5,320,598 discloses a dry-state iontophoretic drug delivery device that has drug and electrolyte reservoirs that are initially in a non-hydrated condition. The device has a liquid containing pouch or breakable capsules that contain water or other liquid, the liquid being releasable by disrupting the liquid containers prior to use. Commercial manufacture of a device utilizing this disclosure would be complex.

U.S. Pat. No. 5,385,543 also discloses a dry-state iontophoretic drug delivery device that has drug and electrolyte reservoirs. The disclosed device includes a backing layer with at least one passageway therethrough that allows the introduction of water or other liquids into the drug and electrolyte reservoirs prior to use followed by joining the reservoirs to the electrodes. The patent teaches that by joining the reservoirs to the electrodes after hydration, delamination problems are reduced.

No commercial products utilizing the technology disclosed either in the '598 or the '543 patents have been produced.

A different approach to the shelf storage stability problem is disclosed in U.S. Pat. No. 5,817,044. In this disclosure, the device is divided or otherwise separated into at least two portions, with one portion containing the electrode reservoir and the other containing the drug reservoir, which may include a medication in a dry form. In this disclosure, the user causes the two portions to come into electrical conducting contact with one another to at least partially hydrate one of the reservoirs, by either folding the device to bring the two portions into contact with one another or by removing a barrier dividing the two portions. While this device is somewhat seems to be somewhat easier to use than the devices disclosed in the above patents, there currently is no commercial device that utilizes this disclosure.

International Application WO 98/208869 discloses an iontophoretic device for delivery of epinephrine and lidocaine HCl. The disclosed device includes materials that deter microbial growth and anti-oxidants to enhance the stability of epinephrine. While this disclosure recognizes the need for shelf storage stability and addresses the problem of epinephrine stability by including anti-oxidants, there is no teaching of the need or ability to uniformly load the reservoir-electrode. Again, there is no commercial product based on the information in this disclosure.

A further problem related to production of a successful commercial pharmaceutical product is related to the requirements for accuracy and precision of dosage. In some of the iontophretic drug delivery devices described above, the user or the practitioner is required to perform some action to hydrate the reservoir-electrode and introduce the medicament introduce the medicament to be delivered into the delivery device prior to use. Such operations that depend upon the practitioner or user to charge the medicament into the device under relatively uncontrolled conditions may result in improper dosing. Regulatory requirements for pharmaceutical products generally specify that not only medicaments contain between ninety and one hundred-ten percent of the label claim, but also that the delivery be uniform from sample to sample.

It is well recognized that many medicaments are not stable to conditions necessary for assembly and storage of iontophoretic reservoir-electrodes. A method of accurately and repeatedly loading the medicament and any required stability enhancing excipients during the assembly process of reservoirs useful for passive transdermal drug delivery and reservoir-electrodes for iontophoretic drug delivery devices that was compatible with a mechanized assembly process and also provided a charged reservoir-electrode with satisfactory stability properties would represent an advance to the art of delivery of medicaments. By providing a stable ready-to-use device as disclosed below, the method of the invention substantially eliminates used induced variability due to loading. Summary A method of the present invention for loading a material into a hydrophilic transdermal medicament delivery reservoir includes providing a transdermal delivery device including a backing with an interior surface that has a bibulous reservoir having a patient contact surface disposed on the inside surface. The method of the invention further includes placing a section of an absorbent material on the patient contact surface of the bibulous reservoir, applying a preselected aliquot of a material to be charged into said bibulous reservoir onto the absorbent material and allowing the absorbent reservoir having the absorbent material with the aliquot of the material applied thereto to stand for a sufficient time for the material to be absorbed into the bibulous material, thereby loading the material into the reservoir.

A method of the present invention for loading a material into an iontophoresis reservoir-electrode includes providing an iontophoresis reservoir-electrode including a backing with an interior surface having an electrode thereon and a bibulous reservoir having a patient contact surface with a shape disposed on the interior surface of the backing in electrical contact with the electrode. The method also includes providing a closure sized and shaped to engage the backing for forming a releasable seal to isolate the bibulous reservoir from the ambient environment, the closure is removable from the housing to expose the patient contact surface for use. The provided closure has an inside surface with a section of an absorbent material disposed thereon. The provided section has a first surface with a similar shape to the contact surface of the bibulous reservoir so that when the closure is disposed on the backing, the absorbent material first surface is positioned in intimate physical contact with the contact surface of the reservoir. The method further includes applying a preselected aliquot of a material to the absorbent material on the inside surface of the closure and placing the absorbent material on the patient contact surface of the reservoir. The method also includes allowing the reservoir-electrode with the closure applied thereto to stand for a sufficient time to allow the aliquot of the material to be absorbed into the bibulous reservoir thereby loading the reservoir-electrode.

An iontophoresis reservoir-electrode of the invention includes a backing with an interior surface including an electrode, a bibulous reservoir that has a patient contact surface with a shape disposed on and in electrical contact with the electrode. The reservoir-electrode is charged with a preselected aliquot of a material and has a closure that is sized and shaped to isolate the bibulous reservoir from ambient environment. The closure is removable from the backing to expose the patient contact surface for use. The closure has an inside surface with a section of an absorbent material disposed thereon. The section has a first surface with a similar shape to the contact surface of the bibulous reservoir and with the closure disposed on the backing, the absorbent material first surface is positioned in intimate physical contact with the contact surface of the bibulous reservoir and removed from the patient contact surface of the bibulous material when the closure is removed from the backing.

The device formed by the method of the invention overcomes the problem of reliably applying the correct amount of the desired materials to passive transdermal reservoirs and for iontophoretic devices. Both the medicament and excipients for the active reservoir-electrode or the materials necessary for the return reservoir-electrode are accurately and precisely loaded into the reservoir. Many materials that are suitable for forming the reservoir are cross-inked by the application of ionizing radiation or require application of thermal energy in forming. If the medicaments are mixed with the material before forming or cross-linking, the medicament is exposed to the forming conditions, i.e., ionizing radiation, thermal energy, chemically reactive cross-linking agents and the like, that may adversely effect the medicament. Thus there is a need for a method of loading the transdermal reservoir or the iontophoretic reservoir-electrode after the reservoir is formed. The method of the invention uniformly loads the reservoir-electrode of the invention during the assembly process, improves the efficiency of assembly of both passive transdermal reservoirs and iontophoresis reservoir-electrodes and is compatible with the high-speed assembly line manufacture necessary for a successful commercial product. The method and the device of the invention greatly improve the efficiency of assembly of complete medicament loaded reservoir-electrodes and thus advances the art of iontophoretic drug delivery by making a prefilled ready-to-use device available that fulfills the regulatory requirements of accuracy and precision.

BRIEF DESCRIPTION OF THE FIGURES

FIG. 4 is a flow chart of the method of the invention for preparing a reservoir-electrode charged with medicament; and.

FIG. 5 is a top plan view of the backing web and the closure web.

DETAILED DESCRIPTION

Figure 1:
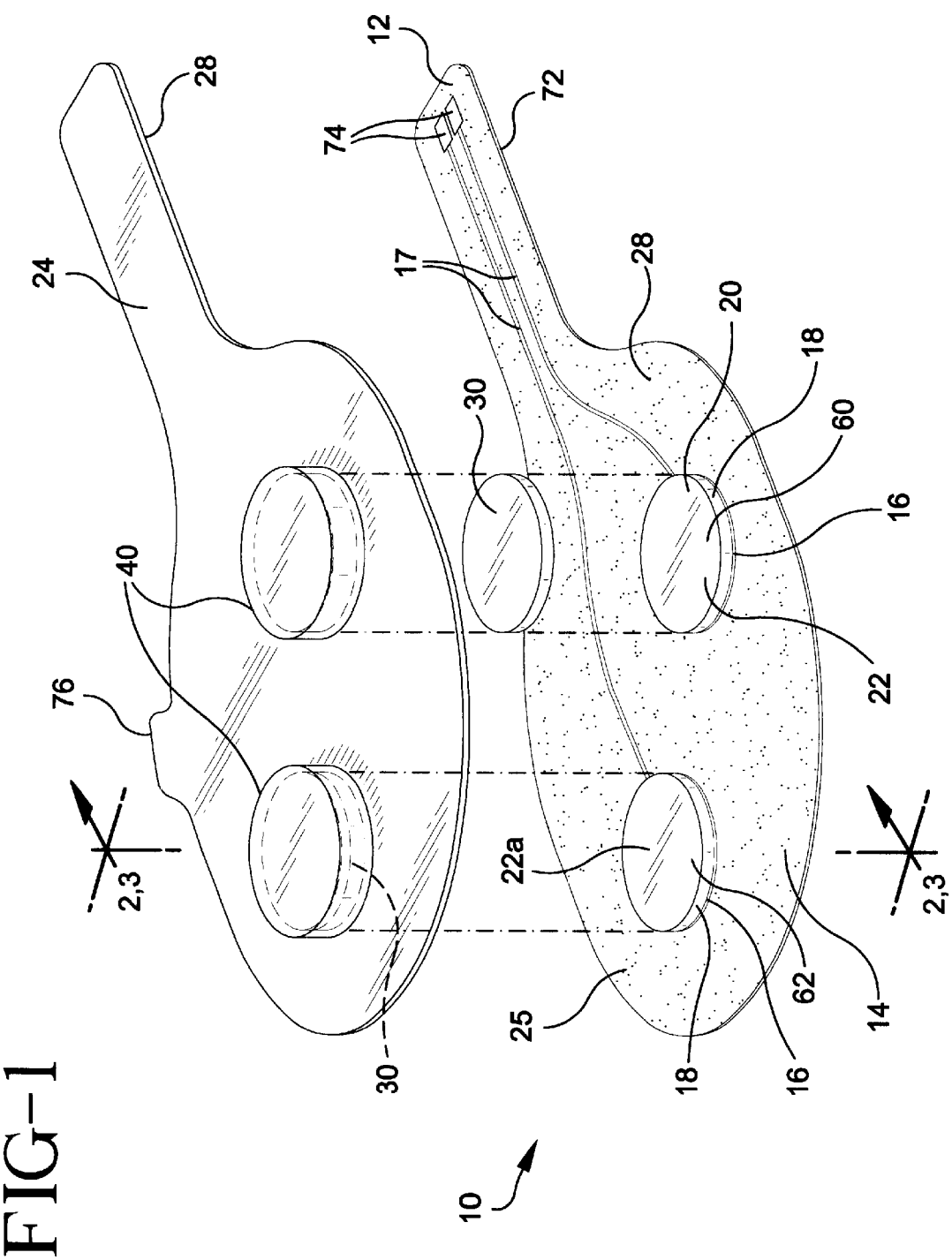
FIG. 1 is an exploded perspective view of the reservoir-electrode unit prepared by the method of the invention.
Figure 2:
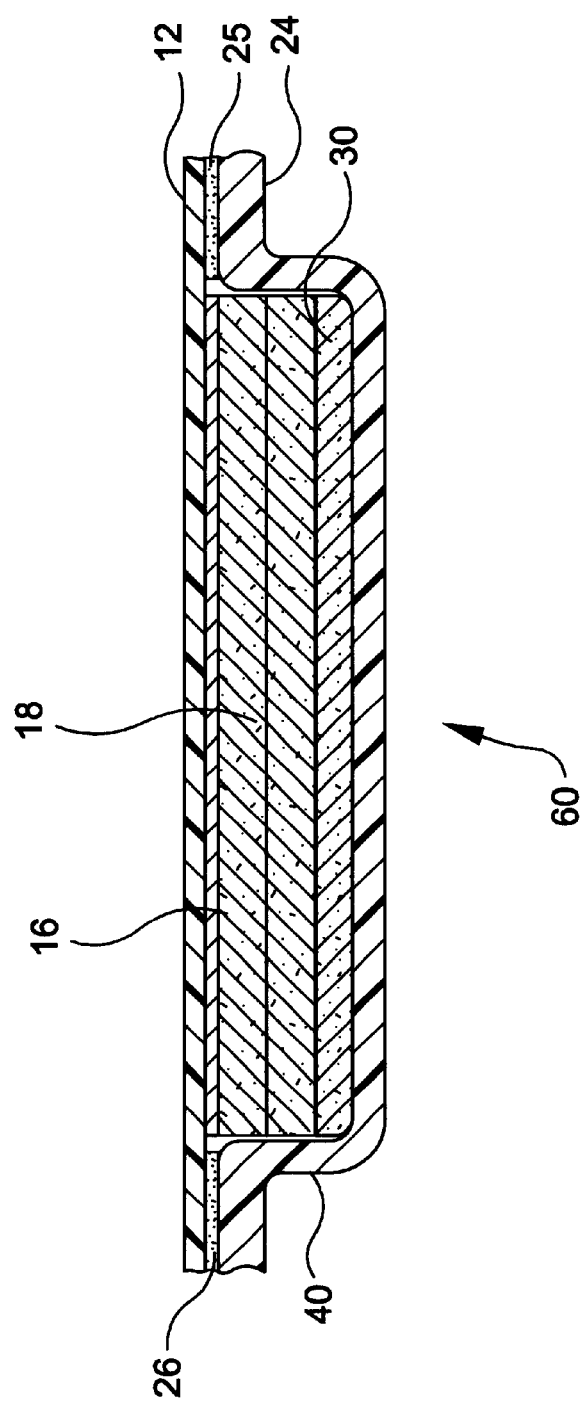
FIG. 2 is a cross-sectional view of a reservoir-electrode of the unit of FIG. 1 taken along the line 2—2.

While this invention is satisfied by embodiments in many different forms, there is shown in the drawings and is herein described in detail, a preferred embodiment of the invention with the understanding that the present disclosure is to be considered exemplary of the principles of the invention and is not considered to limit the invention to the embodiment illustrated. The scope of the invention is measured by the appended claims and their equivalents.

Referring to FIGS. 1–5, a method of the present invention for loading a material into an iontophoresis reservoir-electrode 10 includes providing iontophoresis reservoir-electrode 10 of the invention including a backing 12 with an interior surface 14 that has an electrode 16 disposed thereon, a bibulous reservoir 18 having a patient contact surface 20 with a shape 22 disposed on interior surface 14 of backing 12 in electrical contact with electrode 16. The method also includes providing a closure 24 sized and shaped to engage backing 12 for forming a releasable seal 26 to isolate bibulous reservoir 18 from the ambient environment, closure 24 is removable from backing 12 to expose patient contact surface 20 for use. Provided closure 24 has an inside surface 28 with a section 30 of an absorbent material disposed thereon. Provided section 30 has a first surface 32 with a similar shape 22 to contact surface 20 of bibulous reservoir 18 so that when closure 24 is disposed on backing 12, absorbent material first surface 32 is positioned in intimate physical contact with patient contact surface 20 of reservoir 18. While it is preferred that section 30 has a similar shape to contact surface 20 of reservoir 18, testing has shown that if section 30 covers at least a portion of or is even larger than contact surface 20, the method of the invention still is applicable. The method further includes applying a preselected aliquot 34 of a material to absorbent material 30 on the inside surface 28 of the closure 24. The method further includes placing closure 24 on backing 12 so that first surface 32 of absorbent material 30 is in intimate physical contact with contact surface 20 of bibulous reservoir 18 and closure 24 forms releasable seal 26 with backing 12. The method also includes allowing reservoir-electrode 10 with closure 24 applied thereto to stand for a sufficient time to allow aliquot 32 of the material to be absorbed into bibulous reservoir 18 thereby loading reservoir-electrode 10. For particular applications, it may be preferred to load reservoir 18 with the aliquot of loading solution prior to placement of the loaded reservoir on backing 12, and this alternative is considered within the scope of the invention.

Preferably, backing 12 is formed from a film or sheet material such as polyethyleneterephthalate (PET) or the like in the form of a first web 36 having a plurality of electrodes 16 spaced apart in electrical isolation thereon. Electrodes 16 are preferably formed as a thin film of the desired shape printed onto interior surface 14 of backing 12 using a conductive ink that includes silver and silver chloride. Closure 24 is preferably a material such as a polyethylene terephthalateglycol (PETG) or the like in the form of a second web 38 with a plurality of recesses 40 formed into closure inside surface 28 to receive sections 30 of the absorbent material in registration with electrodes 16 on first web 36. Recesses 40 may be formed into surface 28 by thermoforming or other equivalent methods of forming. Other film materials such as polyamide, polyvinylchloride, polystyrene and the like may be preferred for particular applications.

Absorbent material 30 may be a polymeric foam, porous polymeric sheeting, absorbent paper, nonwoven or combinations of these materials. The absorbent material should not adversely interact with the material loading solution to induce any decomposition or diminution of potency of any medicament or other agent present in the solution. Preferably, absorbent material 30 is a nonwoven with a basis weight of between about 5 and about 20 mg per cm$^2$ is selected. Nonwoven materials having a basis weight lower than about 5 mg per cm apparently have too little structure to provide sufficient void volume to sufficiently retain the aqueous aliquot used in these experiments and those materials having a basis weight greater than about 20 mg per cm$^2$ have sufficient void volume to accept the aqueous aliquot, but tend to retain more of the aliquot, rather than allow transfer of it to the reservoir than is desirable. For aliquots of other materials and other concentrations, other absorbent materials having different void volumes and properties may be preferred. Suitable nonwoven materials include, but are not limited to, nonwovens formed from viscose rayon, polyethylene, polyester, polyamide, polypropylene, PET, and combinations of these polymers. A nonwoven thermal bonded mixture of viscose-rayon and polyethylene, sold by Freudenberg, under the trade name Vilmed M-1561 with a basis weight of about 10 mg per cm$^2$ is preferred because of its properties of absorbency and release of the aqueous medicament solutions, as well as its wide acceptance in other medical applications, although other similar materials are available and also are useful.

Preferably, absorbent material 30 is fixedly attached to closure 24 so that when closure 24 is removed from backing 12 to expose patient contact surface 20 for use, absorbent material 30 is cleanly removed from the patient contact surface of the reservoir. Heat staking, ultrasonic welding or adhesive bonding are suitable techniques for fixedly attaching the absorbent material to closure 24. Ultrasonic welding is preferably used for the preferred nonwoven absorbent material and the preferred PETG closure, because no additional materials such as adhesives are used that may adversely interact with the loading ingredients.

For particular applications, absorbent material 30 may be preferably placed directly on patient contact surface 20 of the reservoir for the addition of the aliquot and removed directly from patient contacting surface 20 of the reservoir by the user. Additionally, for particular applications, it may be desirable to charge absorbent material 30 with the preselected aliquot of the material prior to placement on the patient contacting surface of the reservoir. These alternative sequences of loading and placement are considered within the scope of the method of the invention.

A releasable adhesive 25 is applied to one or the other of the backing 12 or closure 24 to form releasable seal 26. For the preferred PET and PETG materials used for the backing and the closure, a pressure sensitive adhesive material is preferably applied to backing 12. Surface 28 of the closure material is treated with a material such as silicone to facilitate adhesive release of closure 24 from the backing 12. A preferred adhesive material, polyisobutylene based and qualified for medical applications, is available from Adhesive Research. The preferred material has sufficient adhesion to a patient's skin that, once closure 24 is removed and applied to the patient, adhesive 25 forms a releasable bond with the patient's skin that serves to hold reservoir-electrode 10 onto the patient for the delivery of the medicament.

Preferably, absorbent reservoir 18 is formed from a hydrophilic material, such as a bibulous hydrophilic cross-linked polymeric material, that has an alkali metal salt, preferably sodium chloride or other physiologically acceptable alkali metal salt uniformly distributed therethrough to substantially eliminate any corrosion of the electrode caused by formation of salt gradient concentrations during the loading of the reservoir-electrode. Suitable materials for forming reservoir 18 include, but are not limited to, gum agar, hydroxethylcellulose, locust bean gum, pectins, polyacrylamide, polyethylene glycol, poly(ethyleneoxide), polyvinyl alcohol, poly(vinylpyrolidone), combinations thereof and the like. Preferably, the bibulous hydrophilic cross-linked polymeric material of reservoir 18 has a patient contact surface 20 and another surface 21 that is adhesively adherent to electrode 16. Preferably, patient contact surface 20 of reservoir 18 is releasably adhesively adherent when applied to the area of a patient's skin. A preferred reservoir 18 is formed from the cross-linked poly(vinylpyrolidone) that has a cohesive strength and forms an adhesive bond with a bond strength between surface 21 of the polymeric material to electrode 16 that is greater than the cohesive strength of the polymeric material. Additionally, an adhesive bond strength of patient contact surface 20 of preferred polymeric reservoir 18 material to the applied area of the patient is less than the cohesive strength of polymeric reservoir 18 so that upon removal of reservoir-electrode 10 of the invention from the applied area of the patient, substantially no preferred polymeric reservoir 18 material remains on the applied area of the patient's skin and the hydrophilic reservoir remains substantially intact and adhesively adherent to electrode 16.

The preferred material for forming hydrophilic reservoir 18 is a cross-linked poly(vinylpyrolidone). The preferred material is prepared as a viscous aqueous syrup that incorporates the selected alkali halide, preferably sodium chloride, in the desired concentration. A preferred material for forming hydrophilic reservoir 18 is poly (vinylpyrolidone) (PVP) with a number average molecular weight greater than about 360,000 daltons prior to cross-linking by application of ionizing radiation. A suitable PVP is available from BASF, NJ as PVP K-90F.

Figure 3A:
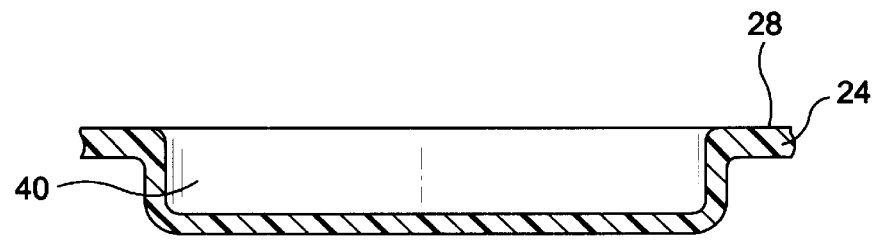
FIGS. 3a–3g are schematic cross-sectional views of the assembly process of the reservoir-electrode unit of FIG. 1.
Figure 3B:
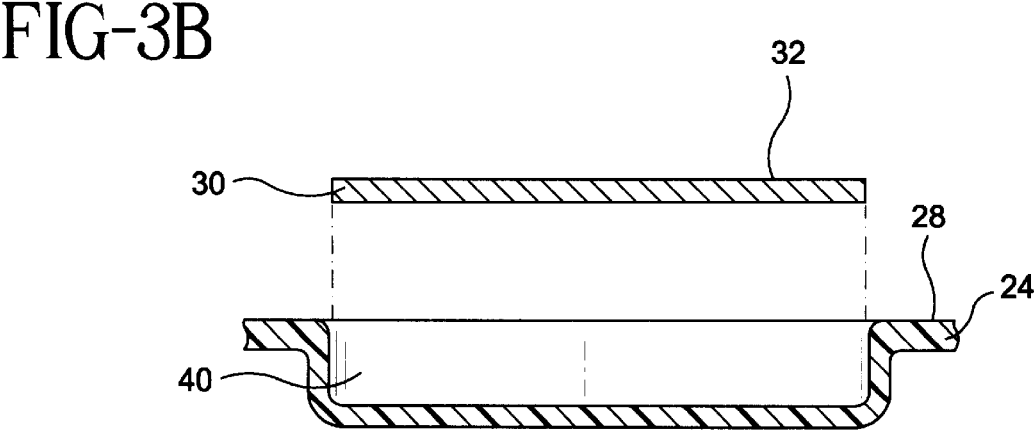
Figure 3C:
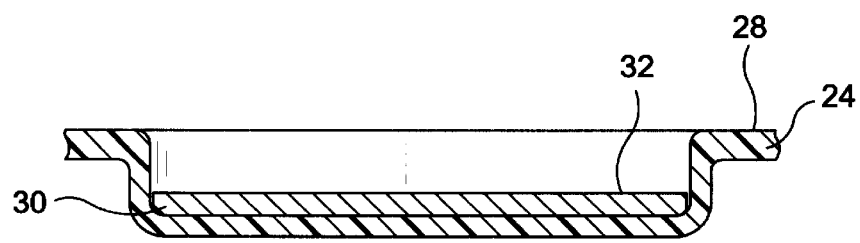
Figure 3D:
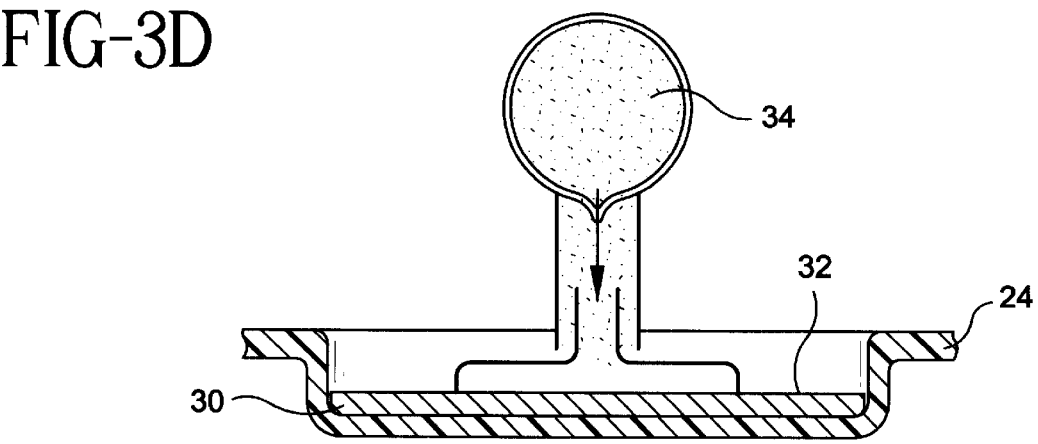
Figure 3E:
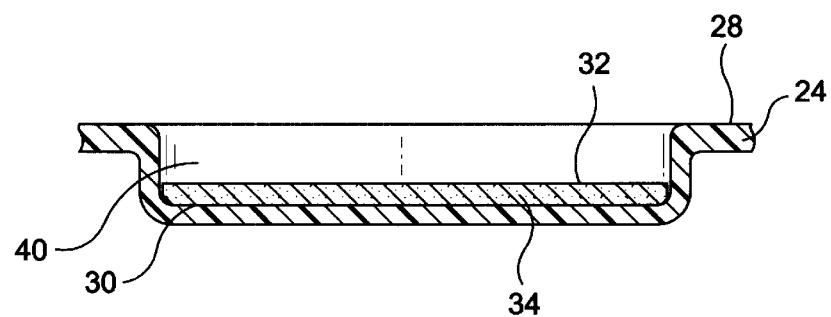
Figure 3F:
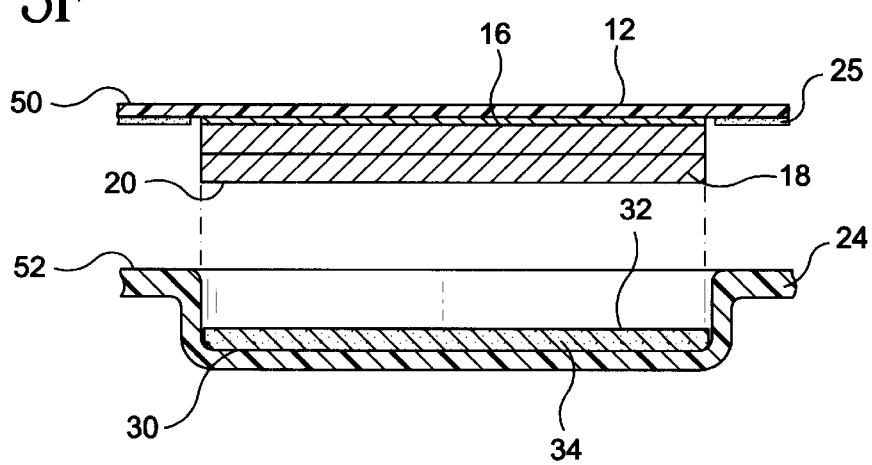
Figure 3G:
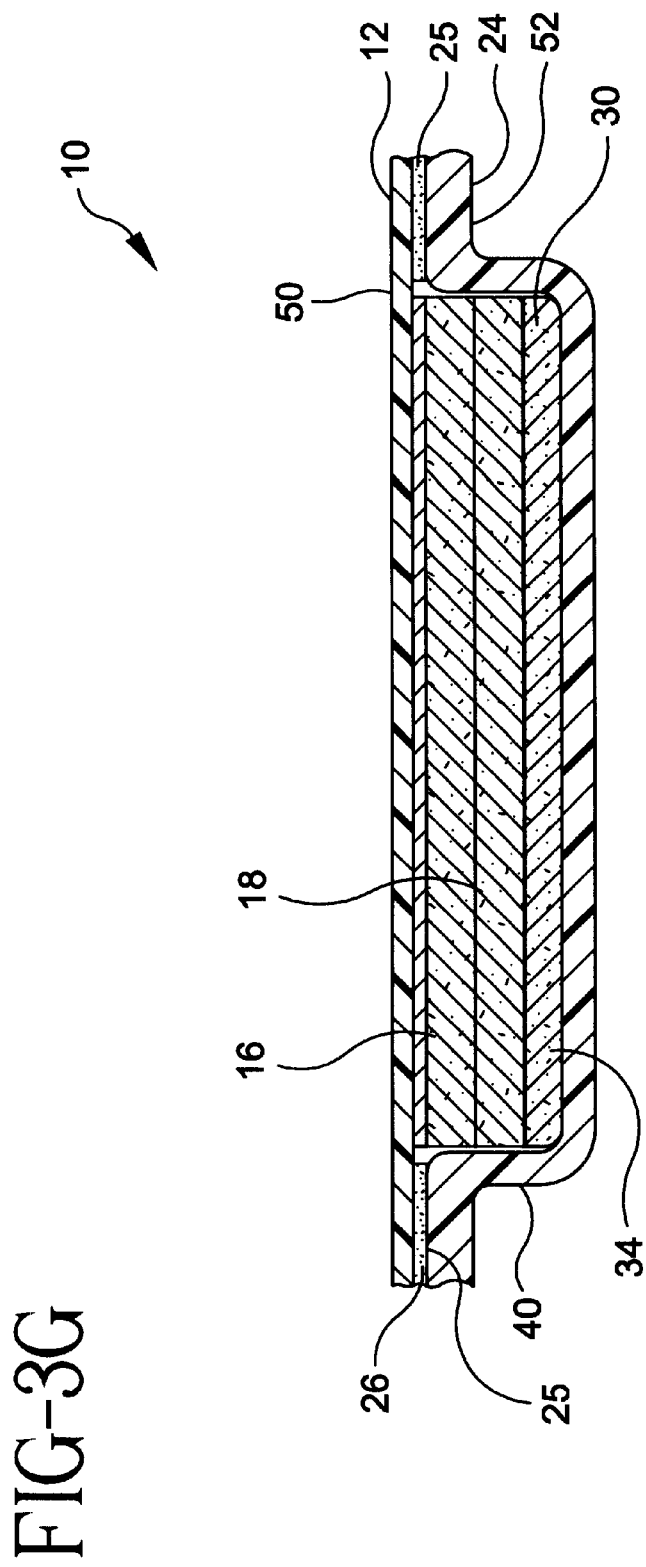
Figure 4:
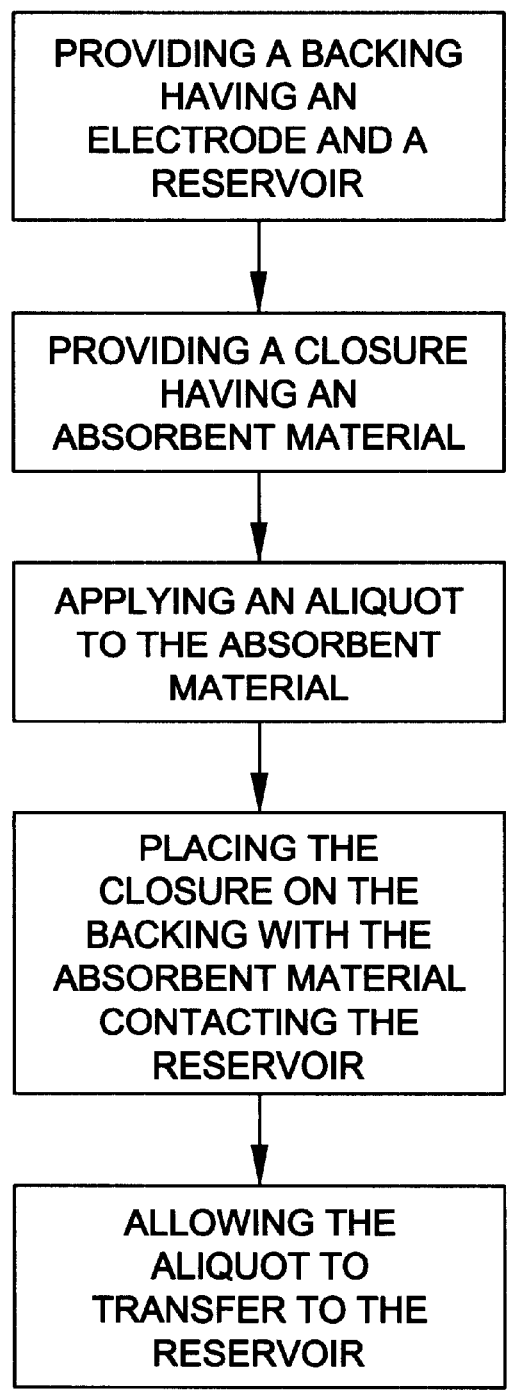

Referring to FIGS. 3a–3g, a schematic cross-sectional illustration of one sequence useful for the formation of the device the invention is shown. A flow chart of the method is illustrated in FIG. 4. Other methods and sequences of assembly of the device of the invention may be envisioned and are considered within the scope of the invention. FIG. 3a illustrates backing 24 with recess 40 formed therein as part of a second web 50. FIG. 3b illustrates section of absorbent material 30 being positioned in recess 40. FIG. 3c shows the absorbent material 30 after fixedly attachment to inside surface 28 of closure 24. In FIG. 3d, aliquot 32 of the material to be charged into reservoir is applied to absorbent material 30. FIG. 3e illustrates the absorbent material with the aliquot in recess 40. FIG. 3f schematically illustrates backing 12 with electrode 16, adhesive 25 and reservoir 18 on first web 52 being positioned in register with absorbent material 30 on closure 24. In FIG. 3g, first web 52 and second web 50 are advanced and moved together to bring reservoir 18 patient contact surface 20 into intimate physical contact with first surface 32 of absorbent material 30 so that aliquot 32 may be absorbed into reservoir 18. As the webs are brought together, adhesive 25 forms releasable seal 26 between backing 12 and closure 24. After seal 26 is formed, a cutting step is used to separate the charged complete reservoir-electrode 10 from the webs.

In the case where the device being formed is a passive transdermal reservoir, all of the steps and illustrations given above are applicable with the exception that backing 12 is provided without electrode 16. In this passive transdermal case, reservoir 18 is preferably disposed directly onto inside surface 14 of backing 12.

FIG. 5 illustrates backing 12 in the form of a first web 52 with a plurality of repeating electrodes 16 printed on interior surface 14. In this preferred embodiment, electrodes 16 have different shapes 22 and 22a that reflect their intended use. In this embodiment, the electrode intended to operate as an anode is designated as 60 and the electrode intended to operate as a cathode is designated as 62. Anode 60 and cathode 62 with respective electrode traces 17 are disposed in electrical isolation from each other as repeating units 70 on web 52. Electrode traces 17 extend on a connection section 72 to connectors 74 to facilitate attachment into a power source (not shown). Closure 24 is also shown in the form of a web 54 with a plurality of recesses 40 having shapes 22 and 22a similar to and in register to anode 60 and cathode 62. The preferred placement of adhesive 25 about electrodes 16 is also shown. Closure 24 preferably includes a tab 76 to facilitate removal of closure 24 from backing 12 to expose the patient contact surface for use.

Production of a commercial scale preferred iontophoretic product is based on the method of the invention with the assembly of unit 70, best seen in FIG. 1, including anode 60, cathode 62, their respective electrode traces 17, reservoirs 18, closure 24 with absorbent material 30 in recess 40 with aliquot 32 being delivered into absorbent material 30 prior to forming adhesive seal 26, shown in FIG. 3G, on webs 50 and 52, as illustrated in FIG. 5. Aliquot 32 may be delivered onto absorbent material 30 as a preselected amount by a coarse or fine spray, dropping, or other similar ways of controlled delivery of fluid onto a surface. Once the assembly process is completed, the individual complete and charged units are ready to be placed in a final package and shipped.

In a preferred product based on the method of the invention, anode 60 is loaded with an aliquot of at least one medicament that is capable of being transported into a patient's body as a positive ion. The term medicament as used in this disclosure is intended to include any therapeutic agent or combination of therapeutic agents capable of being ionized and transported into the body by an electric current. In the case where the therapeutic agent to be transported forms a negative ion, the active electrode is the cathode 62 and the anode 60 would serve as the return electrode. The composition of the aliquots of loading solutions and operation of the active electrode as the cathode or the anode is determined by the medicaments selected.

An example of a preferred embodiment of the invention is where the material to be loaded and delivered includes two medicaments, lidocaine, as the hydrochloride salt, and epinephrine, as the bitartrate salt. In this example, the active reservoir-electrode, i.e., containing the lidocaine and the epinephrine, is anode 60 because the medicaments being delivered are positive ions. Preferably, in aliquots of loading solution 32, lidocaine hydrochloride is present in an amount between about 50 mg to about 150 mg. Other amounts or other medicaments may be preferred for particular applications. In this specific example, about 100 mg of lidocaine hydrochloride is present. Epinephrine bitartrate is preferably present in an amount equivalent to about one-half to about one and one-half mg, and more preferably about one mg, of the free base. Additionally, sodium chloride, glycerin, sodium metabisulfite, editate disodium, citric acid, phenoxy ethanol, alkyl esters of hydroxybenzoic acid are included as excipients in the preferred example active electrode 60.

The method of the invention facilitates the use of automated assembly equipment to prepare complete finished iontophoretic units. The use of the absorbent material to receive an aliquot of the medicament facilitates the use of adhesive hydrophilic reservoir materials, such as poly (vinylpyrolidone) for reservoir-electrodes. The hydrophilic electrodes are well suited to contain and release ionized medicaments into the body under the influence of applied electric current because they are highly absorbent, adhesive and flexible. A problem with many of these hydrophilic reservoir materials is that, while they are highly absorbent, the rate of absorbency is relatively slow, i.e., they do not rapidly absorb a delivered aliquot when they are loaded. Thus, the conventional commercial manufacture of iontophoretic devices with hydrophilic electrodes is slow and inefficient. If the hydrophilic material is not substantially uniformly charged, portions of the reservoir-electrode may not be fully functional causing incomplete delivery and irritation of the patient's skin. The method of the invention utilizes closure 24, which would be needed in any case just to protect the reservoir-electrode, with section 30, of absorbent material, to initially receive the aliquot of the loading solution and keep substantially all of the aliquot present at the surface of the reservoir for diffusing into the reservoir material for as long as necessary during a portion of the shelf storage period rather than extending the time required for the production of the device. Additionally, absorbent material 30 substantially retains the aliquot of the loading liquid during the assembly sequence and substantially prevents migration of the liquid onto adhesive 25 or on portions of webs 50 and 52 away from its intended target, reservoir 18. Tests of completed products prepared using the method of the invention have shown that the loading process for the preferred lidocaine, epinephrine loaded reservoir-electrode is substantially completed within a few days. Additionally, shelf stability testing at ambient conditions of the completed devices shows acceptable performance, i.e., acceptable drug potency and uniformity assay, of the reservoir-electrodes after more than one year of storage.

The accuracy and precision of delivery of the preselected aliquot by the method of the invention to form charged iontophoretic reservoir-electrodes is demonstrated by an experiment where preferred cross-linked poly(vinylpyrolidone) hydrogel reservoir-electrodes 10 were prepared by the method of the invention utilizing preferred non-woven absorbent material 30 (Vilmed, M-1561) to charge aliquots of aqueous lidocaine HCI, epinephrine bitartrate and excipients into bibulous reservoir 18. In this example, the aqueous aliquot of loading solution contained 103.8 mg of lidocaine, 1.10 mg of epinephrine and excipients. Following the loading procedure, the poly(vinylpyrolidone) reservoir materials were assayed for their lidocaine and epinephrine content according to recognized analytical techniques. The analytical results (n=10 reservoir-electrodes) are shown below in Table I. The results show that the transfer efficiency of the loading solution to reservoir 18 for the lidocaine was 96.4 percent and 93.4 percent for the epinephrine. Additionally, after one month at accelerated aging conditions of 40° C., the results are substantially unchanged.

TABLE I

| Time (months) | Lidocaine (mg) | Epinephrine (mg) |
| --- | --- | --- |
| loading solution | 103.8 | 1.10 |
| zero | 99.98 ± 1.07 | 1.035 ± 0.016 |
| one @ 40° C. | 99.12 ± 0.63 | 1.013 ± 0.026 |

The method of the invention for loading a medicament into iontophoretic reservoir-electrodes is suitable for use as a method for loading reservoirs of passive transdermal devices. Most conventional passive transdermal devices utilize a hydrophobic reservoir material, often a hydrocarbon pressure-sensitive adhesive base such as a polyisobutylene or the like. The active ingredient to be transdermally delivered is mixed with the hydrocarbon base and formed onto the substrate or backing material. Often, this hydrocarbon base is maintained at an elevated temperature prior with aliquots of the base already containing the medicament being formed into the device. While the hydrophobic base is suitable for alkaloids such as scopolamine or small molecules such as nitroglycerine, many other drugs are more stable as salts and are more easily used in a hydrophilic system. Additionally, many medicament materials may not be sufficiently thermally stable to the elevated temperatures used in melting and forming the hydrophobic base. The method of the invention is suitable for loading preselected uniform dosages of a medicament into a hydrophilic reservoir for use in passive transdermal delivery as well as the iontophoretic reservoir-electrodes. The benefits of being able to form a hydrophilic gel reservoir using ionizing radiation, chemical cross-linking agents or thermal energy without subjecting the medicament to these conditions applies equally well to a reservoir intended for passive transdermal delivery.

The method of the invention for loading a medicament into transdermal reservoirs and iontophoretic reservoir-electrodes improves the efficiency of manufacturing devices suitable for commercial distribution. The method of the invention addresses the regulatory requirements for accuracy, precision and repeatability that are needed in a practical commercial product. The improved stability and efficiency of iontophoretic devices manufactured using the method of the invention should facilitate their regulatory approval and result in benefits to the art of delivery of medicaments to patients.

What is claimed is:

1. A method for loading a material into a hydrophilic transdermal medicament delivery reservoir comprises:

providing a transdermal delivery device including a backing having an interior surface comprising a bibulous reservoir having a patient contact surface disposed on said interior surface;

placing a section of an absorbent material on said patient contact surface of said bibulous reservoir;

applying a preselected aliquot of a material to be charged into said bibulous reservoir onto said absorbent material; and allowing said bibulous reservoir having said absorbent material with said aliquot of the material applied thereto to stand for a sufficient time for the material to be absorbed into said bibulous material, thereby loading said material into said reservoir.

2. The method of claim 1 further comprising providing a closure sized and shaped to engage said backing for forming a releasable seal to isolate said bibulous reservoir from ambient environment, said closure engaging said backing after placing and said applying step, said closure being removable from said backing to expose said patient contact surface for use.

3. The method of claim 1 wherein said applying step for applying said aliquot of said material to said absorbent material is performed before said placing step of placing said absorbent material on said patient contact surface of bibulous material.

4. The method of claim 1 wherein said providing step for providing said transdermal delivery device including a backing further comprises said interior surface comprising an electrode, said bibulous reservoir being disposed on and in electrical contact with said electrode.

5. The method of claim 1 wherein said providing step for said reservoir selected from the group consisting of gums, alginates, alkyl and hdroxyalkylalkylcellulose, carbosymethylcellulose, gum agar, hydroxethylcellulose, locust bean gum, pectins, polyacrylamide, polyethylene glycol, poly(ethylene oxide), polyvinyl alcohol, poly(vinylpyrolidone) and combinations thereof.

6. The method of claim 5 wherein said providing step for said reservoir further comprises forming said bibulous reservoir from cross-linked poly(vinylpyrolidone).

7. A method for loading a material into an iontophoresis reservoir electrode comprises:

providing an iontophoresis reservoirelectrode including a backing with an interior surface comprising an electrode, a bibulous reservoir having a patient contact surface with a shape disposed on said electrode and in electrical contact with said electrode;

providing a closure sized and shaped to engage said backing for forming a releasable seal to isolate said bibulous reservoir from ambient environment, said closure being removable from said backing to expose said patient contact surface for use, said closure having an inside surface with a section of an absorbent material disposed thereon, said section having a first surface so that when said closure is disposed on said backing, said absorbent material first surface is positioned in intimate physical contact with said patient contact surface of said reservoir;

applying a preselected aliquot of a material to said absorbent material on said inside surface of said closure;

placing said closure on said backing so that said first surface of said absorbent material is in intimate physical contact with said patient contact surface of said bibulous reservoir and said closure forms said releasable seal with said backing;

allowing said iontophoretic reservoir-electrode having said closure applied thereto to stand for a sufficient time, thereby allowing said aliquot of said material to be absorbed into said bibulous reservoir thereby loading said reservoir-electrode.

8. The method of claim 7 wherein said step of providing said closure having said section of said absorbent material disposed thereon further comprises providing a section of absorbent material having a similar shape to said shape of said patient contact surface of said bibulous reservoir.

9. The method of claim 7 wherein said providing step for said iontophoresis reservoir-electrode further comprises providing said backing in the form of a first web having a plurality of reservoir-electrodes spaced apart thereon.

10. The method of claim 9 wherein said providing step further comprises providing said closure in the form of a second web having a plurality of said sections of absorbent material spaced apart thereon to be in registration with said iontophoresis reservoir-electrodes on said first web.

11. The method of claim 10 wherein said providing step for said closure in the form of said second web further comprises forming a depression in said closure being sized and shaped to accept said section of said absorbent material so that when said aliquot of said loading material is applied to said section, said aliquot is substantially retained about said section.

12. The method of claim 11 wherein said providing step for said first web and said second web further comprises applying a releasable sealing material to one of said first web and said second web so that when said first web and said second web are disposed to said closure is being placed on said backing, said releasable sealing material forms said releasable seal between said first web and said second web.

13. The method of claim 12 further comprising positioning said first web with respect to said second web so that as said first web and said second web are advanced in a direction so that said closure is disposed to form said seal with said backing.

14. The method of claim 13 further comprising at least one cutting step for freeing each of said plurality of reservoir-electrodes each having said closure thereon from said webs as a unit.

15. The method of claim 14 wherein said providing step for said reservoir-electrode further comprises providing at least a first reservoir-electrode and a second reservoir-electrode, each reservoir-electrode comprising an electrode, a bibulous reservoir with a patient contact surface having a shape, said reservoir-electrodes being disposed on said interior surface of said backing.

16. The method of claim 15 wherein said providing step for said reservoir-electrode further comprises said first reservoir-electrode and said second reservoir-electrode being arranged in pairs electrically isolated from one another on said backing.

17. The method of claim 16 wherein said applying step for said reservoir electrode further comprises applying a first aliquot to said section of absorbent material in registration with said first reservoir-electrode and a second aliquot, different from said first aliquot, to said section of said section of absorbent material in registration with said second reservoir-electrode.

18. The method of claim 17, wherein said providing step for said reservoir-electrode further comprises providing said first reservoir-electrode and said second reservoir-electrode having a different shape from each other.

19. The method of claim 7 wherein providing step for said closure further comprises selecting said absorbent material from the group consisting of paper, polymeric foam, porous polymeric sheeting, non-woven matrices and combinations thereof.

20. The method of claim 18 wherein said selecting step further comprises selecting a non-woven material having a basis weight between about 5 mg and 20 mg per $cm^2$.

21. The method of claim 20 wherein said providing step for said closure further comprises fixedly attaching said absorbent material to said inside surface of said closure, so that when said closure is removed from said backing to prepare for a use of said iontophoretic reservoir-electrode, said absorbent material is removed as a part of said closure thereby exposing said patient contact surface of said reservoir for application to the patient's skin.

22. The method of claim 7 wherein said applying step for said material to said absorbent material further comprises applying at least one medicament in an aqueous solution.

23. The method of claim 22 wherein said applying step for said material further comprises applying an aqueous solution having materials selected from the group consisting of lidocaine hydrochloride, epinephrine bitartrate, sodium chloride, glycerin, phenoxy ethanol, citric acid, sodium meta-bisulfite, edetate disodium and alkyl esters of para-hydroxy benzoic acid and combinations thereof.

24. A method for preparing a charged reservoir-electrode unit comprising a first reservoir-electrode disposed to operate as an anode and a second reservoir-electrode disposed to operate as a cathode comprises:

providing a backing material in the form of a first web having an interior surface;

providing a first reservoir-electrode having a first surface area, said first reservoir-electrode comprising an first electrode disposed on said interior surface of said backing, a first bibulous reservoir having a first patient contact surface having a shape being disposed on and in electrical contact with said first electrode;

providing a second reservoir-electrode having a second surface area, said reservoir-electrode comprising a second electrode disposed on said interior surface of said backing in electrical isolation from said first electrode, a bibulous second reservoir having a second patient contact surface having a shape being disposed on and in electrical contact with said second electrode;

providing a closure in the form of a second web disposed to engage said backing for forming a releasable seal to isolate said first and said second bibulous reservoirs from ambient environment, said closure being removable from said housing to expose said patient contact surfaces for use, said closure having an inside surface with sections of an absorbent material in register with said first and said second reservoir-electrodes disposed thereon, each said sections having a first surface with a similar shape to each of said patient contacting surfaces of said bibulous reservoirs so that when said closure is disposed on said backing, said absorbent materials first surfaces are each positioned in intimate physical contact with said contact surface of said reservoirs;

applying a preselected aliquot of a first material to said section in register with said first reservoir and an aliquot of a second material to said section in register with said second reservoir;

advancing said first web and said second web in a direction so that said first surface of said absorbent materials are in intimate physical contact with said patient contact surfaces of said bibulous reservoirs and said closure forms said releasable seal with said backing;

cutting each of said first and said second reservoir-electrodes each having said closure thereon from said webs as a unit; and allowing said iontophoretic reservoir-electrode unit having said closure applied thereto to stand for a sufficient time, thereby allowing said aliquots of said materials to be absorbed into said bibulous materials thereby loading said reservoir-electrodes.

25. An iontophoresis reservoir-electrode comprising:

a backing with an interior surface comprising an electrode, bibulous reservoir loaded with a preselected aliquot of a material and having a patient contact surface with a shape disposed on said electrode and in electrical contact with said electrode;

a closure sized and shaped to engage and being disposed on said backing for forming a releasable seal to isolate said bibulous reservoir from ambient environment, said closure being removable from said backing to expose said patient contact surface for use, said closure having an inside surface with a section of an absorbent material disposed thereon, said section having a first surface with a similar shape to said patient contact surface of said bibulous reservoir with said closure disposed on said backing, so that said absorbent material first surface is positioned in intimate physical contact with said contact surface of said bibulous reservoir when said closure is disposed on said backing and removed from patient contact surface of said bibulous reservoir when said closure is removed from said backing.

* * * * *

UNITED STATES PATENT AND TRADEMARK OFFICE
CERTIFICATE OF CORRECTION

PATENT NO. : 6,496,727 B1
DATED : December 17, 2002
INVENTOR(S) : Bernhard et al.

It is certified that error appears in the above-identified patent and that said Letters Patent is hereby corrected as shown below:

Column 2,
Lines 43-44, which now reads "introduce the medicament introduce the medicament" should read -- introduce the medicament --.

Column 3,
Line 65, which now reads "cross-inked" should read -- cross-linked --.

Column 5,
Line 9, which now reads "aliquot 32" should read -- aliquot 34 --.
Line 42, which now reads "5 mg cm apparently" should read -- 5 mg $cm^2$ apparently --.

Column 7,
Lines 59 and 61, which now reads "aliquot 32" should read -- aliquot 34 --.

Column 8,
Line 21, which now reads "loading solution 32" should read -- loading solution 34 --.

Column 10,
Line 39, which now reads "said reservoir selected" should read -- said reservoir further comprises forming said bibulous reservoir from hydrophilic polymeric material selected --.

Signed and Sealed this

Twenty-fourth Day of June, 2003

JAMES E. ROGAN
*Director of the United States Patent and Trademark Office*